(12) United States Patent
Horvath et al.

(10) Patent No.: US 10,022,504 B2
(45) Date of Patent: Jul. 17, 2018

(54) SEPARABLE HUB POST OF PEN NEEDLE

(75) Inventors: Joshua Horvath, Sparta, NJ (US);
Joseph Brizzolara, Hamburg, NJ (US);
Charles Hwang, Wellesley, MA (US);
James Bates, Sparta, NJ (US); Keith Knapp, Warwick, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/261,197

(22) PCT Filed: Sep. 15, 2010

(86) PCT No.: PCT/US2010/002505
§ 371 (c)(1),
(2), (4) Date: Apr. 2, 2012

(87) PCT Pub. No.: WO2011/034576
PCT Pub. Date: Mar. 24, 2011

(65) Prior Publication Data
US 2012/0179115 A1 Jul. 12, 2012

Related U.S. Application Data (60) Provisional application No. 61/244,001, filed on Sep. 18, 2009.

(51) Int. Cl.
*A61M 5/32* (2006.01)
*A61M 5/34* (2006.01)

(52) U.S. Cl.
CPC .......... *A61M 5/3205* (2013.01); *A61M 5/344* (2013.01); *A61M 5/3293* (2013.01);
(Continued)

(58) Field of Classification Search
CPC .. A61M 5/3205; A61M 5/344; A61M 5/3293;
A61M 2005/3206;
(Continued)

(56) References Cited

U.S. PATENT DOCUMENTS 1,683,350 A * 9/1928 Hein ..................... A61M 5/344
285/322
1,740,459 A * 12/1929 Hein ..................... A61M 5/344
604/242
(Continued)

FOREIGN PATENT DOCUMENTS

CN 88101341 A 11/1988
DE 2900827 * 7/1980
(Continued)

OTHER PUBLICATIONS

EPO English Translation of DE2900827, dated Apr. 4, 2016.*
(Continued)

*Primary Examiner* — Aarti B Berdichevsky
*Assistant Examiner* — Laura Schell
(74) *Attorney, Agent, or Firm* — Dickinson Wright, PLLC (57) ABSTRACT

A pen needle (101) for use with a drug delivery device (100) includes a hub body (113) having internal threads (216) to receive the drug delivery device (100). A post (121) is connected to the hub body (113). A needle (103) is rigidly fixed to the post (121). The post (121) is separable from the hub body (113) such that the needle (103) is removed with the post (121). The fluid path is not disturbed by such removal because the entire needle (103) is removed with the post (121). Removal of only the post (121) and needle (103) reduces the volume of waste required for disposal, thereby increasing the effective capacity of a sharps container.

8 Claims, 12 Drawing Sheets

(52) U.S. Cl.
CPC .............. *A61M 2005/3206* (2013.01); *A61M 2005/3279* (2013.01); *Y10T 29/49815* (2015.01); *Y10T 29/53991* (2015.01)

(58) Field of Classification Search
CPC .......... A61M 2005/3279; A61M 5/343; A61M 5/345; A61M 5/346; A61M 5/348; A61M 5/349; A61M 5/32; A61M 5/34; A61M 2005/342
USPC .................... 604/240–243, 264, 272–274
See application file for complete search history.

(56) References Cited

U.S. PATENT DOCUMENTS

| | | | |
|---|---|---|---|
| 3,916,893 A * | 11/1975 | De Felice | .............. 604/193 |
| 4,907,600 A | 3/1990 | Spencer | |
| 5,584,817 A * | 12/1996 | van den Haak | ...... A61M 5/322 |
| | | | 604/110 |
| 5,829,589 A | 11/1998 | Nguyen | |
| 5,944,700 A | 8/1999 | Nguyen | |
| 5,964,737 A | 10/1999 | Caizza | |
| 6,158,314 A | 12/2000 | Thead | |
| 2001/0014792 A1 * | 8/2001 | West et al. | ............... 604/239 |
| 2006/0032769 A1 | 2/2006 | Erickson | |
| 2006/0229562 A1 | 10/2006 | Marsh et al. | |
| 2007/0149924 A1 | 6/2007 | Marsh | |
| 2011/0224640 A1 * | 9/2011 | Kuhn | ................... A61M 5/288 |
| | | | 604/414 |

FOREIGN PATENT DOCUMENTS

| | | |
|---|---|---|
| DE | 3339705 A1 | 5/1985 |
| EP | 1 440 703 A2 | 7/2004 |
| FR | 2 623 403 A1 | 5/1989 |
| GB | 978 570 A | 12/1964 |
| GB | 2214082 A | 8/1989 |
| JP | S49127494 A | 12/1974 |
| JP | H01178264 A | 7/1989 |
| JP | H04500016 A | 1/1992 |
| JP | H08512214 A | 12/1996 |
| JP | 3039408 U | 7/1997 |
| JP | H11146914 A | 6/1999 |
| JP | 2000102614 A | 4/2000 |
| JP | 2001190668 A | 7/2001 |
| JP | 2007-209508 A | 8/2007 |
| WO | 2007/032354 A1 | 3/2007 |
| WO | 2008/008694 A2 | 1/2008 |

OTHER PUBLICATIONS

Chinese Office Action dated Jun. 3, 3013.
European Search Report issued in Application No. 10817549.8-1662 dated Oct. 15, 2013.

* cited by examiner

SEPARABLE HUB POST OF PEN NEEDLE

CROSS REFERENCE TO RELATED APPLICATION

This application claims the benefit under 35 U.S.C. § 119(e) of U.S. Provisional Application Ser. No. 61/244,001, filed Sep. 18, 2009, the entire content of which is hereby incorporated by reference.

FIELD OF THE INVENTION

The present invention relates to a pen injection device for use in a drug delivery system in which the hub post and needle are separable from the hub body of the pen needle, thereby reducing sharps disposal volume and increasing the effective capacity of the sharps container. More particularly, the present invention relates to a hub post that is removably connected to the hub body of the pen needle to facilitate separation of the hub post and needle from the hub body. The present invention also relates to a device for separating the needle and hub post from the hub body of the pen needle.

BACKGROUND OF THE INVENTION

Medication delivery pens are hypodermic syringes used for self-injection of precisely measured doses of medication. Pens are widely used, for example, by diabetics to dispense insulin.

A typical prior art medication delivery pen includes a cartridge that contains a volume of liquid medication sufficient for several doses. The dose is delivered into a tissue area, such as the intramuscular tissue layer, the subcutaneous tissue layer, or the intradermal tissue layer.

Figure 1:
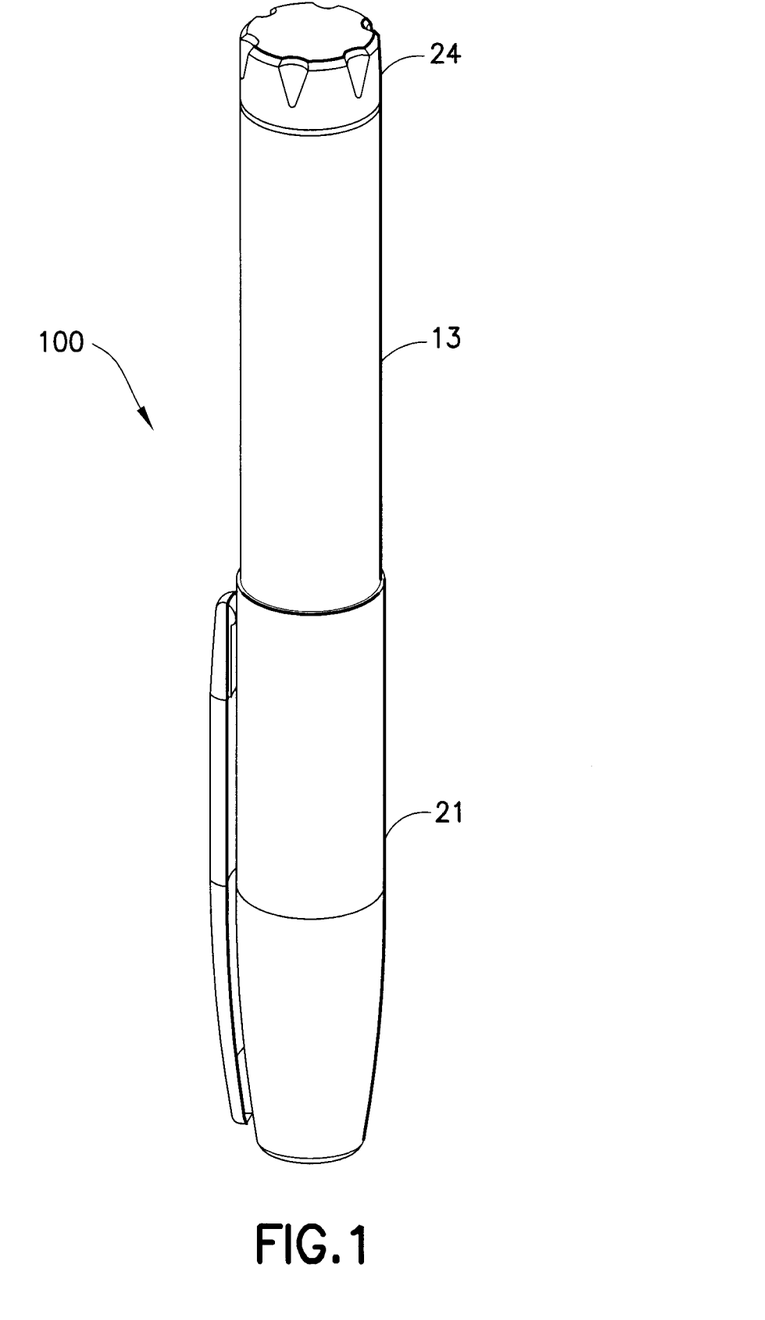
FIG. 1 is a perspective view of an assembled existing pen injection device.
Figure 2:
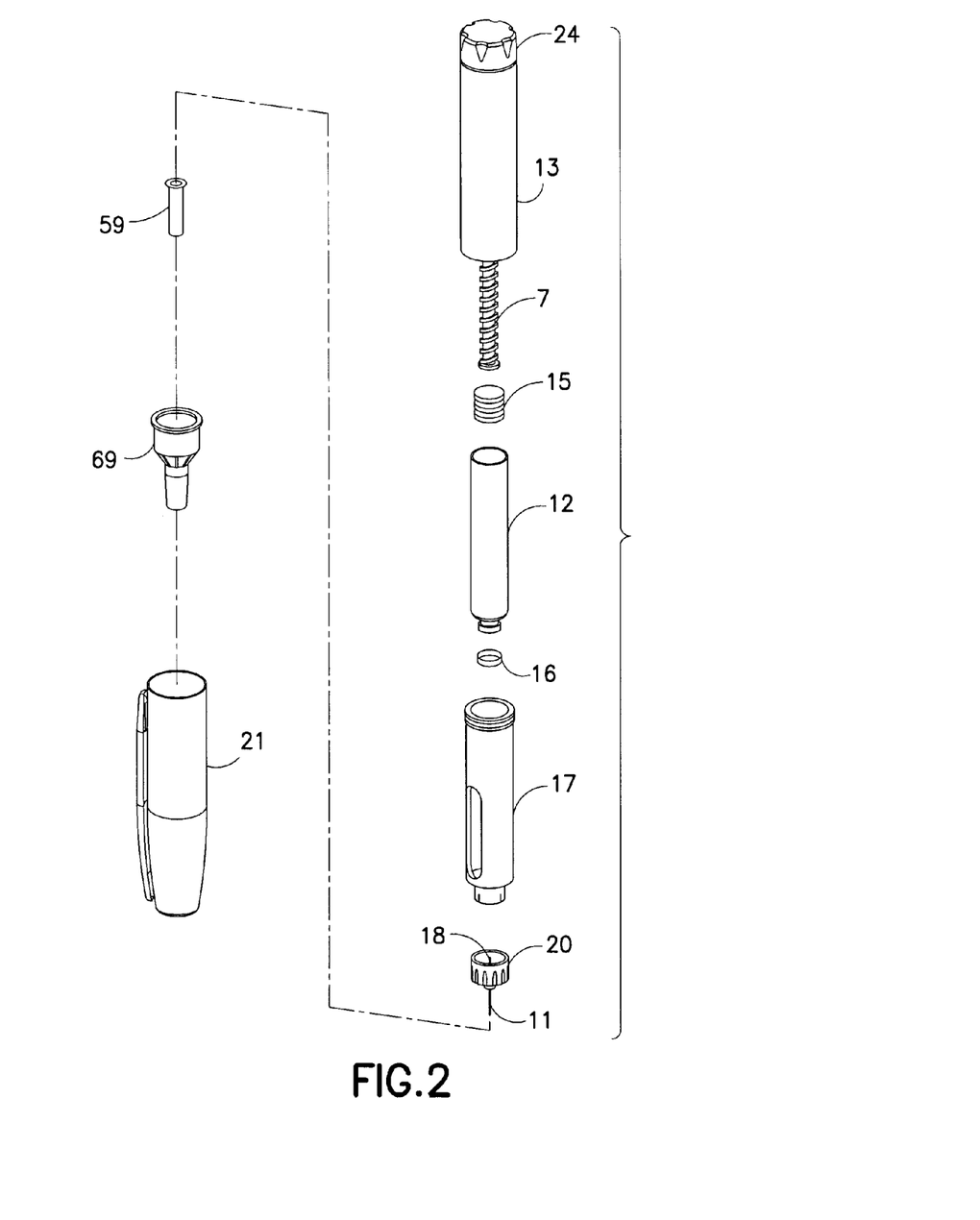
FIG. 2 is an exploded perspective view of the components of the pen injection device of FIG. 1.

Following an injection with a drug delivery pen 100, as shown in FIGS. 1 and 2, the pen needle, which includes the hub 20 and needle 11, are unthreaded from the lower housing 17 and disposed in a sharps container. Current sharps containers for residential use have an internal volume of approximately 1.4 quarts (1.32 liters) and can accommodate approximately 300 pen needles. Accordingly, a need exists for reducing the size of the sharps requiring disposal, thereby increasing the capacity of the sharps container. Additionally, by reducing the size of the sharps requiring disposal, the volume of the sharps container may be decreased while increasing its capacity.

Furthermore, when separating the needle from the hub of the pen needle, the drug fluid path should not be disturbed to prevent the generation of potentially biohazardous aerosol particles. Accordingly, a need exists for removing the needle from the hub of a pen needle without disturbing the drug fluid path.

SUMMARY OF THE INVENTION

In accordance with an aspect of the present invention, a hub post and needle are separable from the hub of the pen needle, thereby reducing the size of sharps requiring disposal:

In accordance with another aspect of the present invention, a sharps separating device has an inlet port for removing a hub post and needle from the hub of the pen needle.

In accordance with yet another aspect of the present invention, a sharps container has a sharps separating device for removing a hub post and needle from the hub of the pen needle.

The foregoing objects are attained by providing a pen needle for use with a drug delivery device. The pen needle includes a hub body having internal threads to receive the drug delivery device. A post is connected to the hub body. A needle is rigidly fixed to the post. The post is separable from the hub body such that the needle is removed with the post. The fluid path is not disturbed by such removal because the entire needle is removed with the post. Removal of only the post and needle reduces the volume of waste required for disposal, thereby increasing the effective capacity of a sharps container.

The foregoing objects are also attained by providing a method of reducing the amount of waste generated by a pen needle used for an injection with a drug delivery device. A needle and a post are separated from a hub of a pen needle such that an entirety of the needle is separated from the pen needle. The needle and the post are properly disposed of in a sharps container, thereby reducing the amount of waste associated with a used pen needle.

These and other objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which.

Throughout the drawings, like reference numbers will be understood to refer to like parts, components and structures.

DETAILED DESCRIPTION OF THE EXEMPLARY EMBODIMENTS

The following description and details of exemplary embodiments of the present invention, while generally disclosed in a typical drug delivery pen as shown in FIGS. 1 and 2, could more broadly apply to a needle and hub assembly for use in conjunction with, or incorporated onto, other injection devices such as syringes and infusion devices. The assembly and operation of a typical drug delivery pen 100, as shown in FIGS. 1 and 2, is described in U.S. Pat. No. 7,465,264, issued on Jan. 12, 2010, which is hereby incorporated by reference in its entirety.

Pen injection devices, such as the exemplary drug delivery pen 100, as shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the drug delivery pen 100 in a shirt pocket, purse or other suitable location.

FIG. 2 is an exploded view of an exemplary drug delivery pen shown in FIG. 1. The dose knob/button 24 has a dual purpose and is used to both set the dosage of the medication to be injected and to inject the dosed medicament via the lead screw 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used such as attaching to the cartridge. To protect a user, or anyone who handles the pen injection device 100, an outer shield 69, which attaches to the hub 20, covers the hub. An inner shield 59 covers the patient needle 11 within the outer shield 69. The inner shield 59 can be secured to the hub 20 to cover the patient needle 11 by any suitable means, such as an interference fit or a snap fit. The outer shield 69 and inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18, but does not move with respect to the medicament cartridge 12. The stopper 15 is axially displaceable within the medicament cartridge 12 while maintaining a fluid tight seal.

Figure 3:
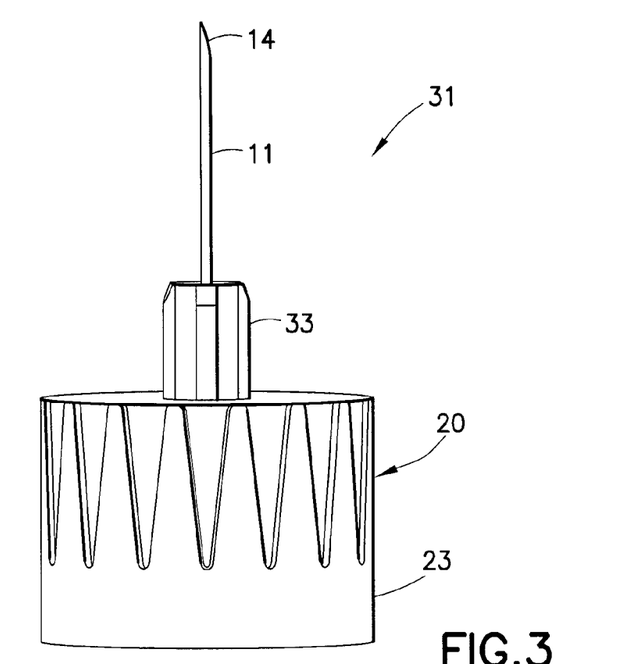
FIG. 3 is a perspective view of a pen needle of the pen injection device of FIGS. 1 and 2.

A typical pen needle 31 is shown in FIG. 3. A hub 20 includes a hub body 23 to which a hub post 33 is connected. The hub body 23 and the hub post 33 are integrally formed as one piece. The needle 11 is connected to the hub 20, with a proximal end disposed externally thereof. An internal portion of the hub body 23 is threaded, as shown in FIG. 2, to removably connect the pen needle 31 to the lower housing 17.

Figure 4:
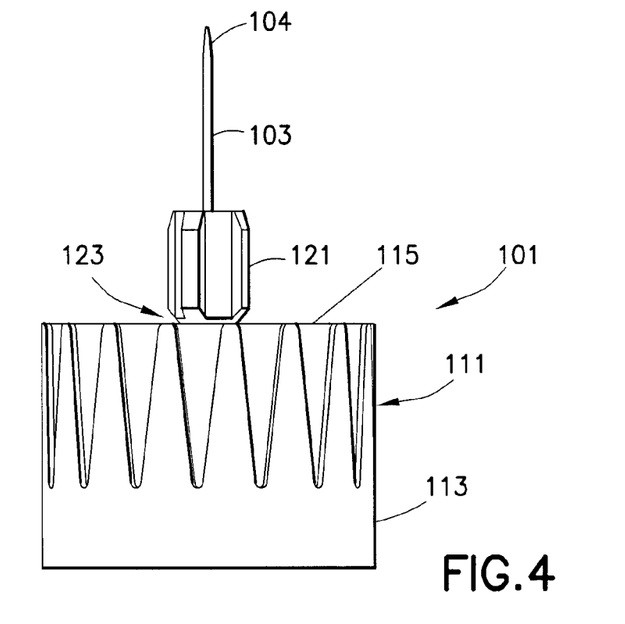
FIG. 4 is an elevational view of a pen needle having a thin cross-section in accordance with an exemplary embodiment of the present invention.
Figures 5, 6:
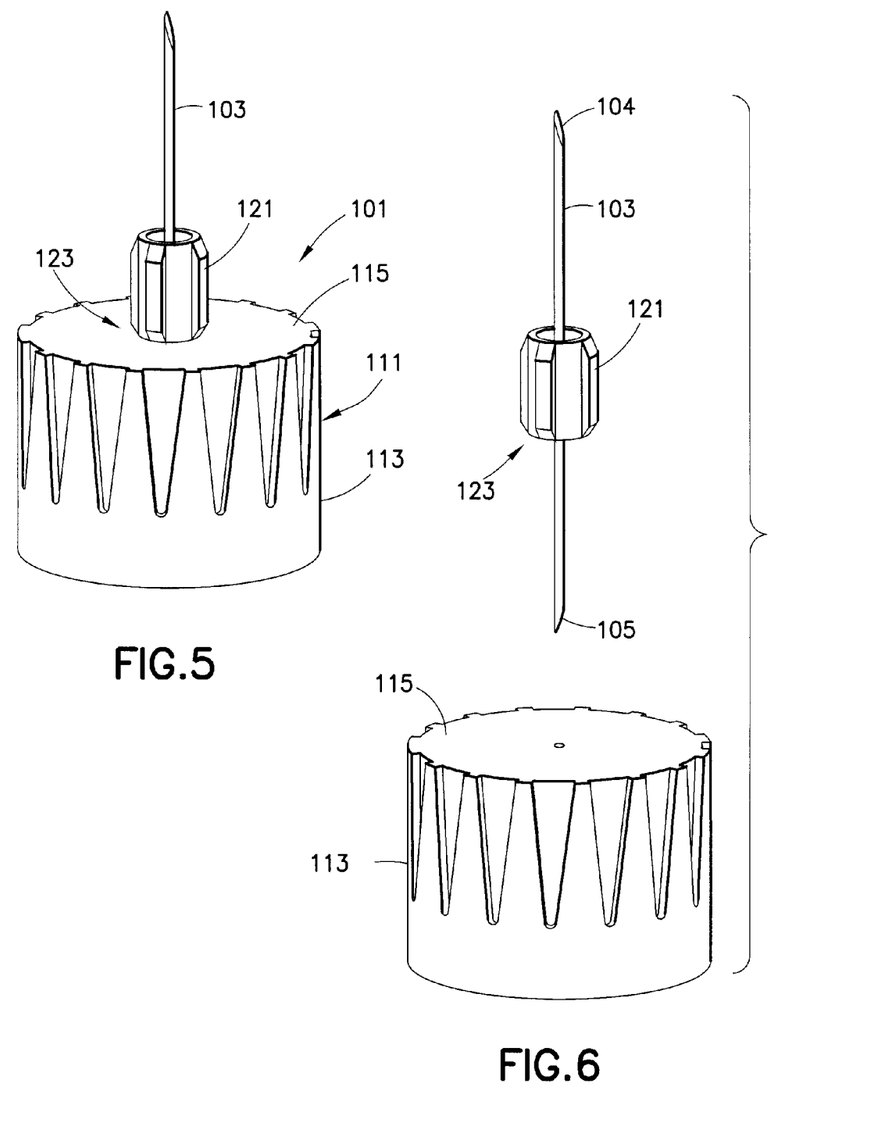
FIGS. 5 and 6 are perspective views of the pen needle of FIG. 4 before and after separation of the hub post and needle from the hub body.

An exemplary embodiment of a pen needle 101 in accordance with an exemplary embodiment of the present invention is shown in FIGS. 4-6. The hub 111 includes a hub body 113 to which a hub post 121 is connected. The hub body 113 and the hub post 121 are integrally formed as one piece. The hub post 121 extends outwardly from a substantially planar surface 115 of the hub body 113. A needle 103 is secured to the hub 111 in any suitable manner. A proximal, or patient, end 104 of the needle is disposed externally of the hub post 121. An internal portion of the hub body 113 is threaded to facilitate connecting the hub body to the lower housing 17 (FIG. 2) of a pen injection device 100.

The cross-sectional thickness of the hub post 121 in an area 123 proximal to the surface 115 of the hub body 113 is reduced, as shown, thereby providing a breakaway area for facilitating separation of the hub post 121 and the needle 103 from the hub body 113, as shown in FIG. 6. The reduced cross-sectional thickness of the hub post 121 allows for separation of the hub post in the area 123 of reduced thickness. The cross-sectional thickness of the remaining portion of the hub post 121 is greater than that of the reduced cross-sectional thickness area 123. The thinner cross-sectional area 123, proximate where the hub post 121 meets the planar surface 115 of the hub body 113 weakens the hub post 121 to allow separation of the hub post from the hub body, such as by gripping and twisting the hub post with a suitable tool. The hub body 113 remains connected to the lower housing 17 (FIG. 2) of the pen injection device 100, such that the pen injection device no longer contains any sharp parts. Additionally, the entire needle 103, from the proximal end 104 to a distal, or non-patient, end 105, is removed with the hub post 121, such that the fluid path is not disturbed.

Figure 7:
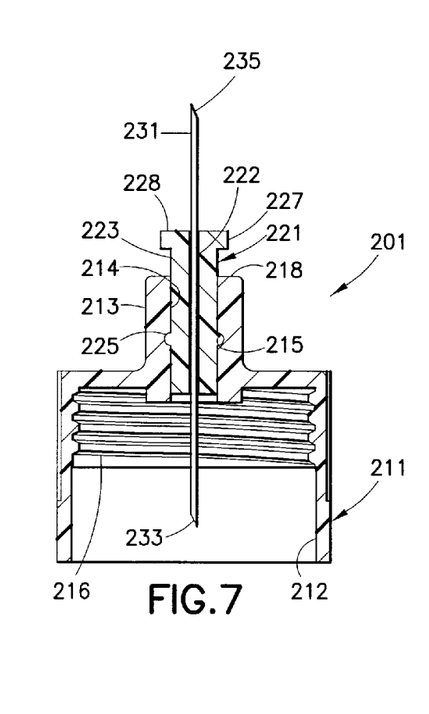
FIG. 7 is an elevational view in partial cross-section of a pen needle having a concentric retaining ring in accordance with another exemplary embodiment of the present invention.
Figure 8:
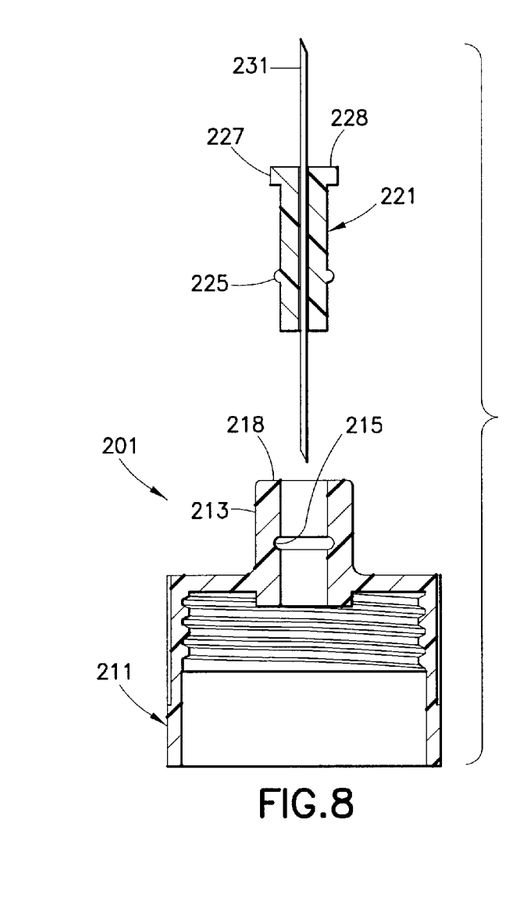
FIG. 8 is an elevational view in partial cross-section of the pen needle of FIG. 7 in which the hub post and hub body have been separated.

In other exemplary embodiments of the present invention shown in FIGS. 7-12, a hub post is removably connected to the hub body so that it can be separated without breaking. In FIGS. 7 and 8, a pen needle 201 includes a hub post 221 removably connected to a hub body 211. The hub body 211 has a projection 213 for removably receiving the hub post 221. An internal surface 214 of the hub projection 213 has a substantially concentric retaining groove 215. An internal surface 212 of the hub body 211 has threads 216 to connect the hub body to the lower housing 17 (FIG. 2).

An outer surface 223 of the hub post 221 has a substantially concentric ring 225, adapted to be received within the retaining groove 215 of the hub projection 213. An opening 222 through the entire length of the hub post 221 receives the needle 231, such that a distal, or non-patient, end 233 is disposed within the hub body 211 and a proximal, or patient, end 235 is disposed externally of the hub post 221. The engagement between the concentric ring 225 and the retaining groove 215 limits the insertion depth of the hub post 221 in the hub projection 213. A flange 227 is disposed at a free end 228 of the hub post 221. Alternatively, the flange 227 can be disposed on the outer surface 223 of the hub post 221 between the concentric ring 225 and the free end 228, and can be disposed to abut the free end 218 of the hub projection 213 when the hub post 221 is properly inserted. An adhesive may be used to further secure the hub post 221 in the projection 213 of the hub body 211. The opening 222 may have concentric rings proximal the free end of the hub post 221 to provide a larger surface area for adhesive bonding.

To remove the hub post 221 and needle 231 from the hub body 211, as shown in FIG. 8, the flange 227 of the hub post is gripped with any suitable tool and pulled outwardly away from the hub body. The flange 227 facilitates handling and manipulation of the hub post 221. When an appropriate force is applied, the ring 225 of the hub post 221 exits the retaining groove 215 and causes the hub projection 213 to flex outwardly, thereby allowing the hub post 221 and the needle 231 to be removed from the hub body 211. The hub body 211 can then be reused with a new hub post 221 and needle 231, particularly when an adhesive is not used to further secure the hub post 221 to the hub body 211.

Figure 9:
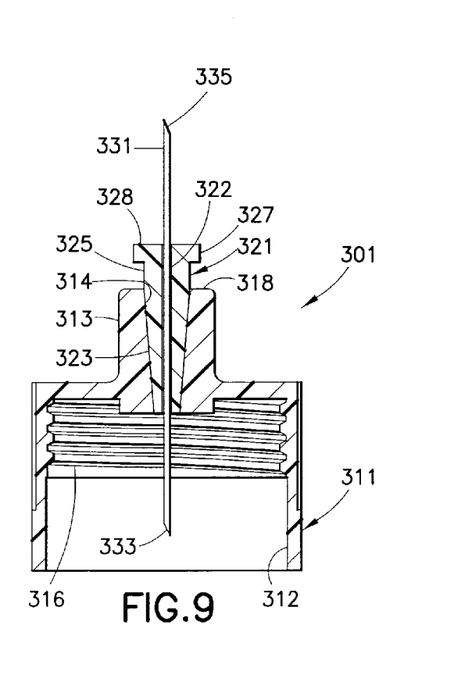
FIG. 9 is an elevational view in partial cross-section of a pen needle having a tapered hub post connected to the hub body in accordance with another exemplary embodiment of the present invention.
Figure 10:
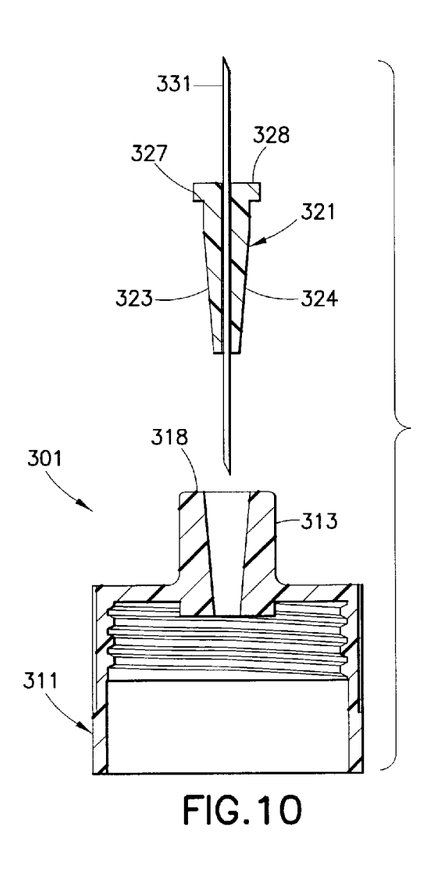
FIG. 10 is an elevational view in partial cross-section of the pen needle of FIG. 9 in which the hub post and hub body have been separated.

In FIGS. 9 and 10, a pen needle hub assembly 301 includes a hub post 321 removably connected to a hub body 311. The hub body 311 has a projection 313 for removably receiving the hub post 321. An internal surface of the hub projection 313 has a tapered portion 314. Preferably, the entirety of the hub projection internal surface 314 tapers inwardly. An internal surface 312 of the hub body 311 has threads 316 to connect the hub body to the lower housing 17 (FIG. 2).

An outer surface 323 of the hub post 321 has a tapered portion 324 corresponding to and received by the tapered portion 314 of the hub projection 313. An opening 322 through the entire length of the hub post 321 receives the needle 331, such that a distal end 333 is disposed within the hub body 311 and a proximal end 335 is disposed externally of the hub post 321. The corresponding taper between the hub post 321 and the opening 322 of the hub projection 313 limits the insertion depth of the hub post 321 in the hub projection 313. A flange 327 is disposed at a free end of the hub post 321. Alternatively, the flange 327 can be disposed on the outer surface 323 of the hub post 321 below the free end 328, and can be disposed to abut the free end 318 of the hub projection 313 when the hub post 321 is properly inserted. An adhesive may be used to secure the hub post 321 in the projection 313 of the hub body 311, or the interference between the tapered surfaces themselves may suffice. The tapered configuration of the hub post 321 ensures proper alignment and positioning of the needle 331.

To remove the hub post 321 and needle 331 from the hub body 311, as shown in FIG. 10, the flange 327 of the hub post is gripped with any suitable tool and pulled outwardly away from the hub body. The flange 327 facilitates handling and manipulation of the hub post 221. When an appropriate force is applied, the hub post 321 is pulled free of the hub projection 313, thereby allowing the hub post 321 and the needle 331 to be removed from the hub body 311. Additionally, an adhesive may be used to bond the hub post 321 to the hub body 311. The hub body 311 can then be reused with a new hub post 321 and needle 331, particularly when an adhesive is not used to bond the hub post 321 to the hub body 311.

Figure 11:
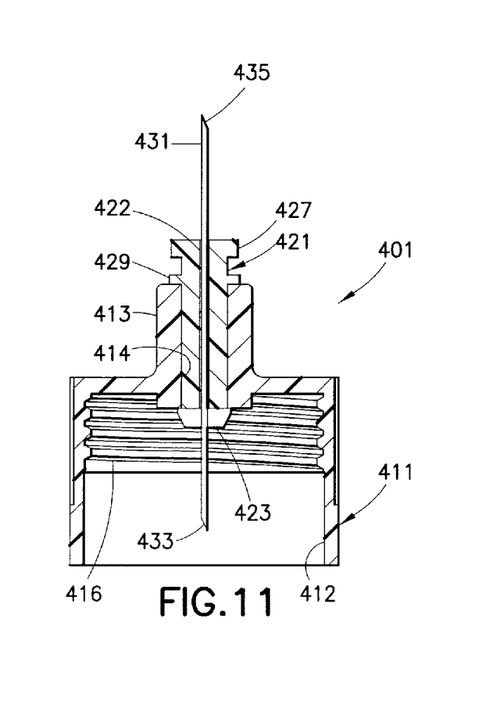
FIG. 11 is an elevational view in partial cross-section of a pen needle in accordance with another exemplary embodiment of the present invention in which locking tabs secure a hub post to the hub body.
Figure 12:
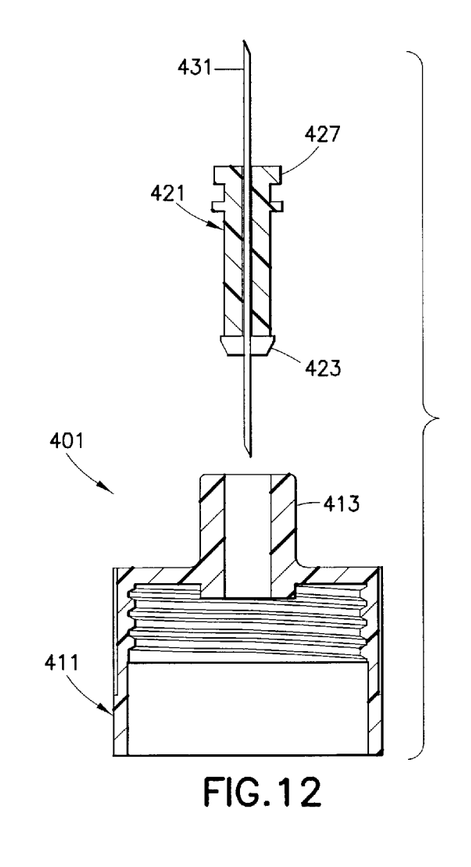
FIG. 12 is an elevational view in partial cross-section of the pen needle of FIG. 11 in which the hub post and hub body have been separated.

In FIGS. 11 and 12, a pen needle hub assembly 401 includes a hub post 421 removably connected to a hub body 411. The hub body 411 has a projection 413 for removably receiving the hub post 421. A passageway 414 extends through the hub projection 413. An internal surface 412 of the hub body 411 has threads 416 to connect the hub body to the lower housing 17 (FIG. 2).

An end of the hub post 421 has a flexible tab 423. The opposite end of the hub post 421 has a first flange 427. An opening 422 through the entire length of the hub post 421 receives the needle 431, such that a distal, or non-patient, end 433 is disposed within the hub body 411 and a proximal, or patient, end 435 is disposed externally of the hub post 421. The hub post 421 is inserted in the passageway 414 in the hub projection 413, which causes the tab 423 to compress. The tab 423 expands to its original size when it is free of the passageway 414. The outer diameter of the tab 423 is larger than the diameter of the passageway 414, such that the hub post 421 is prevented from being withdrawn from the hub projection 413. A second flange 429 is disposed on the hub post 421 to limit movement of the hub post into the hub projection 413. The outer diameter of the second flange 429 is larger than the diameter of the passageway 414, thereby preventing further insertion of the hub post 421 into the hub projection 413. An adhesive may be used to further secure the hub post 421 in the projection 413 of the hub body 411.

To remove the hub post 421 and needle 431 from the hub body 411, as shown in FIG. 12, the first flange 427 of the hub post is gripped with any suitable tool and pulled outwardly away from the hub body. When an appropriate force is applied, the tab 423 is compressed and is pulled through the passageway 414 of the hub projection 413. The hub post 421 and the needle 431 may then be removed from the hub body 411. The hub body 411 can then be reused with a new hub post 421 and needle 411, particularly when an adhesive is not used to bond the hub post 421 to the hub body 411.

Other suitable means may be used to removably connect the hub post to the hub body, such as threadably connecting the hub post to the hub body.

With regard to the hub posts being separated from the hub bodies, as shown in the exemplary embodiments of FIGS. 4-12, the sharps container may have an inlet port into which the hub post is inserted. The inlet port may have means to grip the hub post and separate the hub post from hub body, thereby retaining the hub post and needle within the sharps container. The pen injection device is then removed from the inlet port with the hub body still attached thereto. A flange disposed on the free end of the hub post, as shown in FIGS. 7-12, at 227, 327 and 427, facilitates gripping of the hub post by the inlet port.

Still other suitable means may be used to reduce the size of the sharps waste. Gears may be used to grip the patient end of the needle to extract only the needle from the pen needle hub assembly. An electric current or arc may be applied to the needle, thereby melting the needle. A hole punch may be used to separate the hub post from the hub body. Heat may be applied to the hub, thereby melting the plastic hub and enabling removal of the needle.

As shown in FIGS. 13-18, in another exemplary embodiment of the present invention, a sharps separating device (FIGS. 15-18) includes a blade assembly to cut the hub post 33 from the hub body 23 (FIGS. 13 and 14) of a conventional pen needle.

Figures 13, 14:
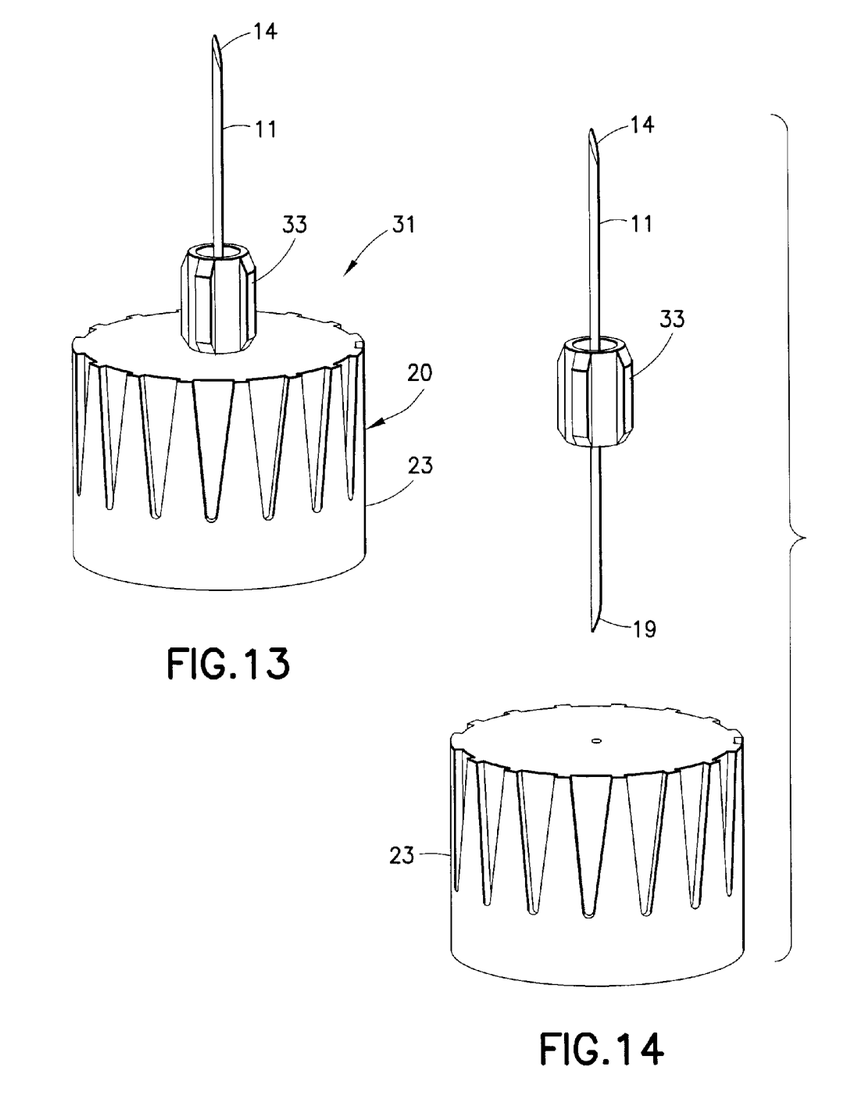
FIG. 13 is a perspective view of the pen needle of the pen injection device of FIGS. 1 and 2.
FIG. 14 is a perspective view of the pen needle of FIG. 13 in which the hub post has been separated from the hub body in accordance with another exemplary embodiment of the present invention.

A sharps separating device 501 (FIG. 15) has a blade assembly 507 including at least one internally disposed blade that cuts the plastic hub post 33 from the hub body 23 when the hub 20 is inserted in the inlet port 505. The needle 11 is not cut so that the entire needle 11, including the proximal, or patient, end 14 and the distal, or non-patient, end 19, is removed with the hub post 33, as shown in FIG. 14. The hub post 33 should be cut as close to the distal end 19 of the needle 11 as possible to minimize the effect of the adhesive used to secure the needle to the hub 20. The sharps separating device 501 has an internal cavity that retains the removed hub post 33 and needle 11. The volume of the internal cavity may be approximately two cubic inches, which can accommodate hundreds of hub posts 33 and needles 11. The sharps separating device 501 meets sharps containment standards and is suitable for mailing to a disposal location.

Existing syringe barrel cutters cut the needle, thereby disturbing the drug fluid path. A sharps separating device according to exemplary embodiments of the present invention does not cut the needle, thereby not disturbing the drug fluid path such that the risk of generating potentially biohazardous aerosol particles is substantially eliminated.

Figure 15:
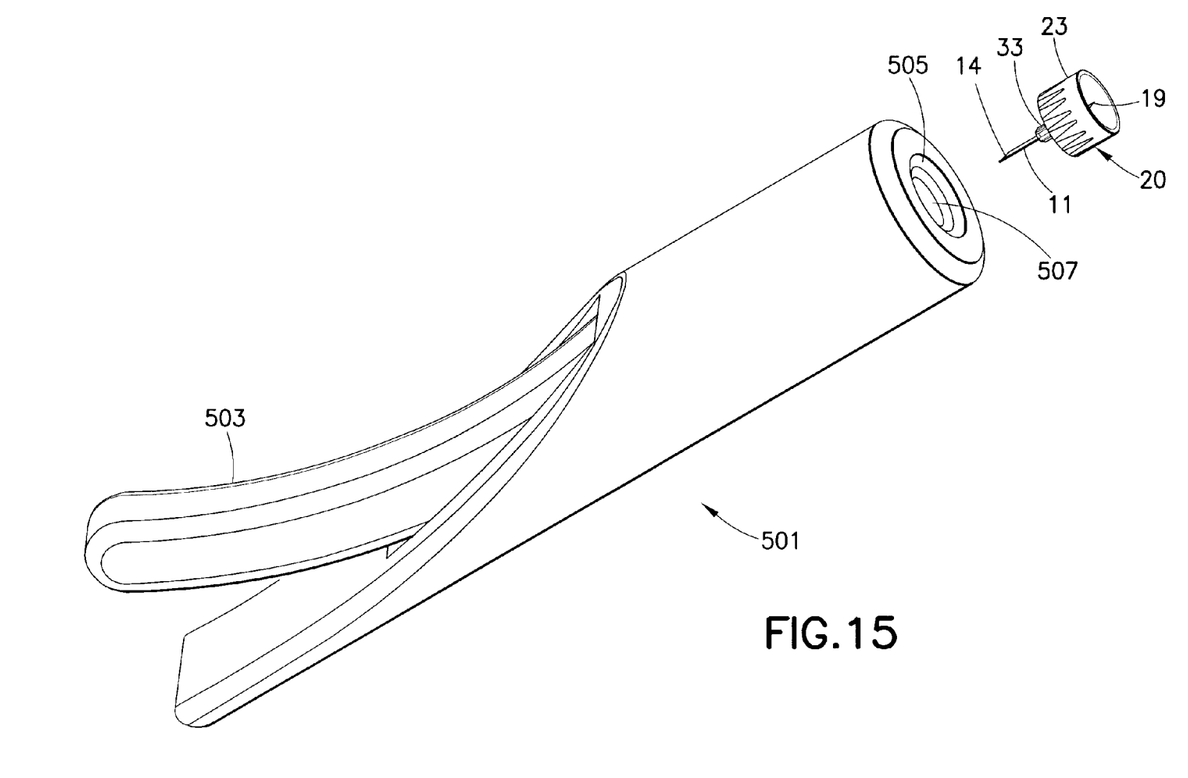
FIG. 15 is a perspective view of a sharps separating device in accordance with another exemplary embodiment of the present invention for separating a hub post and needle from a hub body.

A trigger 503 operates the internally disposed blade assembly 507 of the sharps separating device 501. The internal blade assembly 507 may take the form of a pair of notched blades, a pair of steel plates having offset holes to allow space for the needle, a single blade that moves into engagement with a mechanical stop, or any other suitable blade assembly that separates the hub post 33 from the hub body 23 without cutting the needle 11.

The internal cavity used to collect and store the separated hub posts 33 and needles 11 may be integrated into the sharps separating device, or may be a removable and replaceable container. By having a removable and replaceable container, the sharps separating device is reusable.

Figure 16:
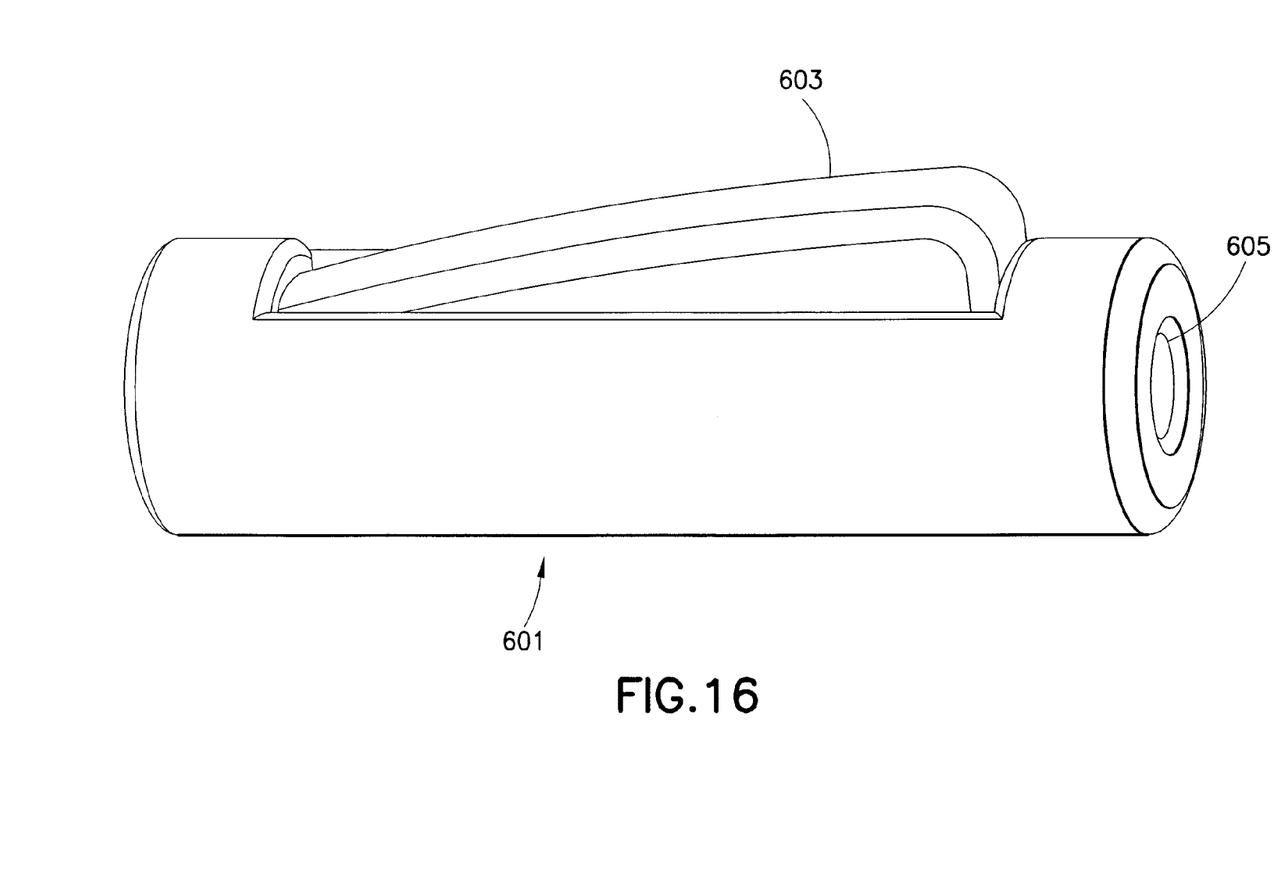
FIG. 16 is a perspective view of a sharps separating device in accordance with another exemplary embodiment of the present invention for separating a hub post and needle from a hub body.
Figure 17:
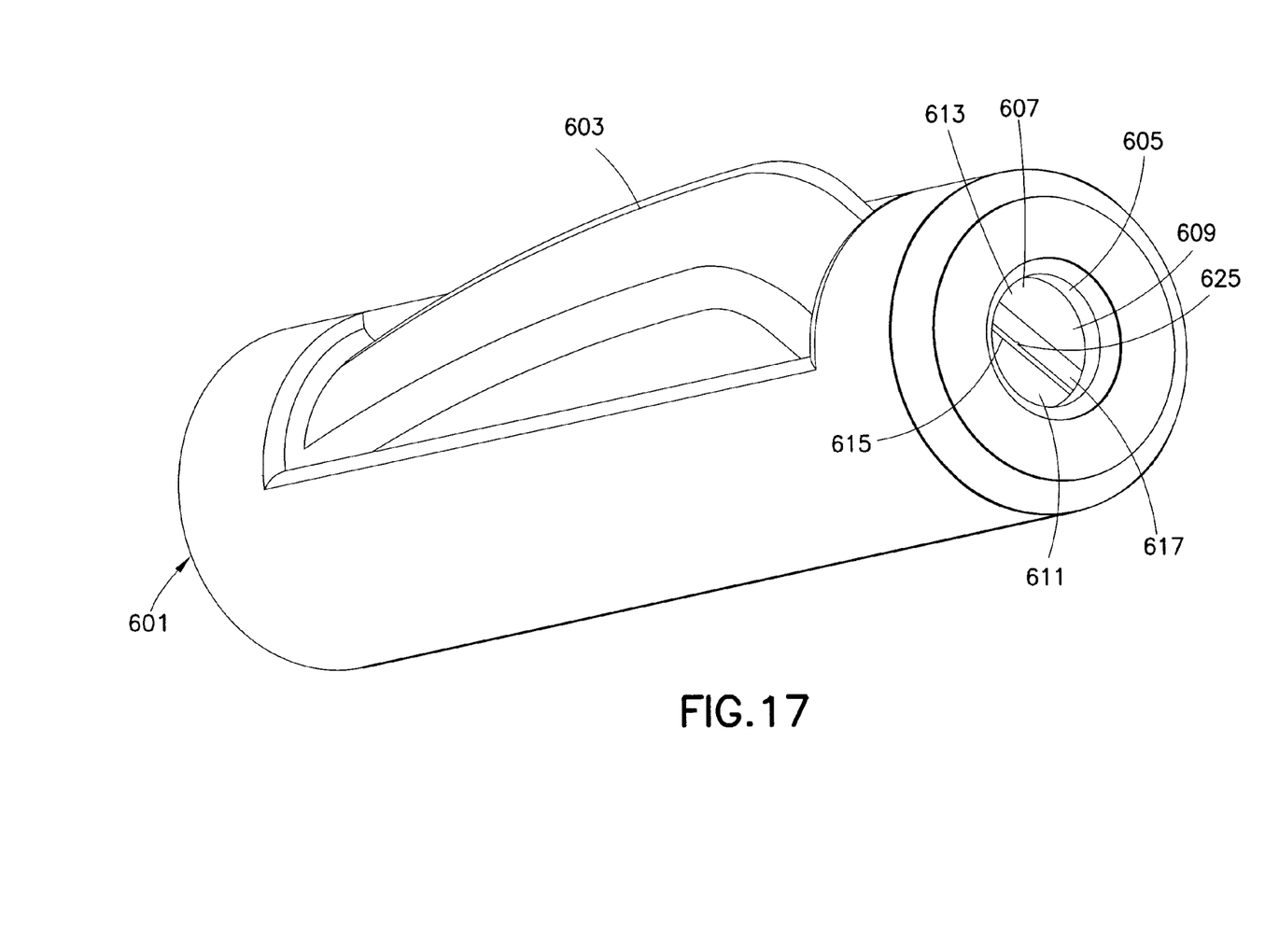
FIG. 17 is a perspective view of the sharps separating device of FIG. 16 showing a pair of blades for separating a hub post needle from a hub body.
Figure 18:
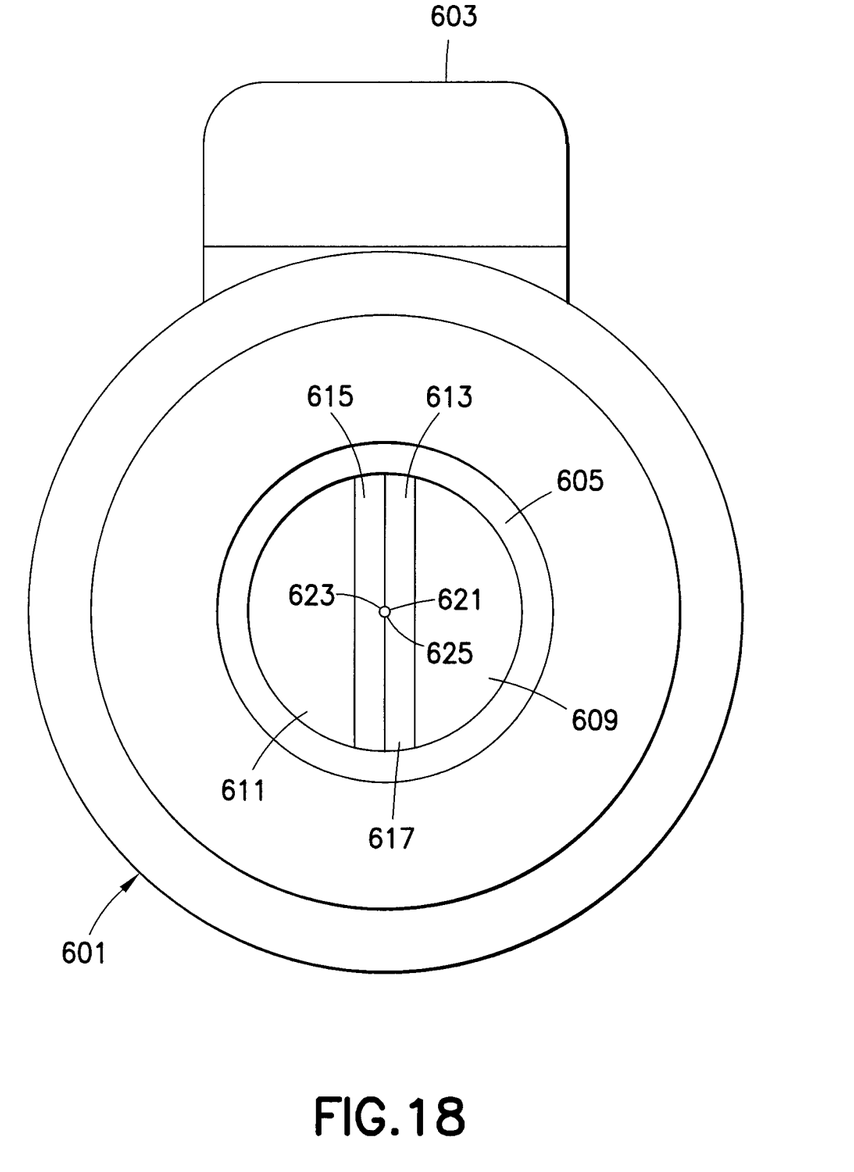
FIG. 18 is a front elevational view of the sharps separating device of FIG. 16.

Another embodiment of a sharps separating device 601 is shown in FIGS. 16-18. The sharps separating device 601 has a trigger 603, an inlet port 605 and a blade assembly 607 disposed within the inlet port 605, and operates in a substantially identical manner to the sharps separating device 501 shown in FIG. 15.

The blade assembly 607 includes a first blade 609 and a second blade 611, as shown in FIGS. 17 and 18. Each of the first and second blades 609 and 611 has a notched portion 613 and 615, respectively, such that a substantially V-shaped portion 617 is formed between the first and second blades. Each of the first and second notched portions 613 and 615 has a cut-out portion 621 and 623, respectively, thereby forming a cutting surface 625 that separates the hub post 33 from the hub body 23 without cutting the needle 11. The substantially V-shaped portion 617 tapers inwardly, i.e., into the sharps separating device 601, to facilitate receiving the larger diameter hub body 23 therein when separating the smaller diameter hub post 33 therefrom. The first and second blades 609 and 611 come together when actuated by the trigger 603 and the cutting surface 625 is sized such that the needle 611 is not cut.

Removing only the hub post and needle reduces the volume of waste required for disposal, thereby increasing the effective capacity of a sharps container. Currently, the entire pen needle 31, as shown in FIG. 3, must be discarded. Existing home sharps containers have an internal volume of approximately 1.4 quarts (1.32 liters), and accommodate approximately 300 pen needles. In exemplary embodiments of the present invention, the capacity of the sharps container can be increased to approximately 15,000 hub posts and needles (29 G×12.7 mm length, approximately). Alternatively, because the capacity of a sharps container is increased, the size of the home sharps container can be decreased while still accommodating more than the current 300 pen needle capacity.

The foregoing embodiments and advantages are merely exemplary and are not to be construed as limiting the scope of the present invention. Various modifications, alternatives and variations will be apparent to those of ordinary skill in the art, and are intended to fall within the scope of the invention as defined in the appended claims and their equivalents.

The invention claimed is:

1. A pen needle for use with a drug delivery device, comprising:
    a hub body having internal threads to receive the drug delivery device, said hub body having a projection extending outwardly proximally from said hub body and integrally formed with said hub body as a one piece member, the hub having a passageway that extends through the entire projection;
    a post removably connected to said projection within said passageway in said hub; and
    a needle rigidly fixed to said post; and
    a first flange at a patient end of the post spaced axially from the projection;
    a second flange on said post axially spaced towards a non-patient end from said first flange and having a diameter larger than the passageway to prevent insertion of the post into the projection past the second flange; and
    a flexible tab disposed at the non-patient end of said post and extending past a non-patient end of the projection and out of the passageway to prevent accidental withdrawal of said post from said projection,
    wherein said post is separable from said hub body such that said needle is removed in its entirety with said post;
    wherein an entire length of said passageway is the same as a length of said post from said second flange to said flexible tab.

2. The pen needle according to claim 1, wherein said hub body has a base and a wall extending outwardly therefrom, and said projection extends from said base in a direction opposite to said wall.

3. The pen needle according to claim 1, wherein said flexible tab has a width larger than that of said passageway.

4. The pen needle according to claim 3, wherein said flexible tab compresses to allow removal of said post from said projection.

5. The pen needle according to claim 1, wherein said second flange has a width larger than that of said passageway to limit insertion of said post in said projection.

6. The pen needle according to claim 1, wherein said post is removed from said projection in its entirety.

7. The pen needle according to claim 1, wherein said second flange is connected to said post to facilitate removal of said post from said projection.

8. The pen needle according to claim 1, wherein when said post is located within said passageway said second flange contacts a patient end surface of said projection and said flexible tab contacts a non-patient end surface of said projection.

* * * * *